United States Patent [19]

Lovell

[11] Patent Number: 5,187,184
[45] Date of Patent: Feb. 16, 1993

[54] INSECTICIDAL AND SYNERGISTIC MITICIDAL COMPOSITIONS

[75] Inventor: James B. Lovell, Pennington, N.J.

[73] Assignee: American Cyanamid Company, Stamford, Conn.

[21] Appl. No.: 634,289

[22] Filed: Dec. 26, 1990

[51] Int. Cl.⁵ .................... A01N 43/36; A01N 43/58
[52] U.S. Cl. .................... 514/406; 514/403; 514/423; 514/424; 514/427; 514/428; 514/429; 514/422; 424/405
[58] Field of Search ............ 514/385, 403, 404, 406, 514/427, 428, 429, 422–424; 424/405

[56] References Cited

U.S. PATENT DOCUMENTS

| | | | |
|---|---|---|---|
| 4,746,354 | 5/1988 | Gehring | 424/405 X |
| 4,804,675 | 2/1989 | Jensen et al. | 424/405 X |
| 4,950,668 | 8/1990 | Ouada et al. | 514/232 |
| 4,965,282 | 10/1990 | Takamura et al. | 514/406 |

FOREIGN PATENT DOCUMENTS 289879  9/1988  European Pat. Off. .

OTHER PUBLICATIONS

Chemical Abstracts, vol. 111, 1989, 111:194576w.
Chemical Abstracts, vol. 111, 1989, 111:111037x.
Farmaco Ed. Sci., 22 (9) pp. 692–697 (Rubessa).
Inl. Famaco Ed. Sc., vol. 38, pp. 369–375 (Baraldi).

*Primary Examiner*—Thurman K. Page
*Assistant Examiner*—Neil Levy
*Attorney, Agent, or Firm*—Peggy A. Climenson

[57] ABSTRACT

This invention relates to new insecticidal and synergistic miticidal compositions containing as essential active ingredients an arylpyrrolecarbonitrile or arylnitropyrrole and an arylpyrazolecarboxamide. The invention also relates to a method for protecting growing plants from infestation and attack by insects and plant mites comprising applying to the foliage and stems of said plants an insecticidally and miticidally effective amount of a composition containing a synergistic mixture of an arylpyrrolecarbonitrile or arylnitropyrrole and an arylpyrazolecarboxamide dispersed in an inert diluent, or sequentially applying to the foliage and stems of plants which are to be protected from attack by insects and plant mites, an arylpyrazolecarboxamide and a synergistically effective amount of an arylnitropyrrole or arylpyrrolecarbonitrile.

8 Claims, No Drawings

INSECTICIDAL AND SYNERGISTIC MITICIDAL COMPOSITIONS

BACKGROUND OF THE INVENTION

It has been stated that when two or more substances in combination show unexpectedly high activity, as for example, miticidal activity, the resulting phenomenon is referred to as synergism. The mechanism of synergism is not fully understood, and quite possibly may differ with different compositions. However, the term "synergism" as used in this application means a cooperative action encountered in combinations of two or more biologically active components in which the combined activity of the two components exceeds the sum of the activities of the components when used alone.

It is an object of this invention to provide new insecticidal and synergistically effective miticidal compositions containing as the essential active ingredients an arylpyrrolecarbonitrile and an arylpyrazolecarboxamide or an arylnitropyrrole and an arylpyrazolecarboxamide.

Arylnitropyrroles and arylpyrrolecarbonitriles are described in copending U.S. patent application Ser. No. 392,495, filed Aug. 11, 1989 incorporated herein by reference thereto, which is a continuation-in-part of U.S. application Ser. No. 208,841, filed Jun. 23, 1988 which is a continuation-in-part of U.S. application Ser. No. 079,545, filed Jul. 29, 1987, now abandoned.

Arylpyrazolecarboxamides are disclosed in the European patent application number 88 106430.7, publication number EPO 289 879.

The above applications describe the disclosed compounds as highly effective insecticidal and acaricidal agents useful for the control of Coleoptera, Diptera, Lepidoptera, Hemiptera, or Orthoptera and Acarina.

SUMMARY OF THE INVENTION

Surprisingly, however, it has now been found that the addition of an arylnitropyrrole or arylpyrrolecarbonitrile to a composition containing an arylpyrazolecarboximide provides superior insect and acarid control at lower levels of the combined active agents than may be achieved with the arylpyrazolecarboxamide, the arylnitropyrrole or the arylpyrrolecarbonitrile applied alone at equal or higher levels than the total amount of active agent used in the combination treatment.

PREFERRED EMBODIMENTS OF THE INVENTION

Advantageously, the arylpyrazolecarboxamide may be combined or formulated with an arylnitropyrrole or arylpyrrolecarbonitrile and the formulation then dispersed in a solid or liquid diluent for application to the insects and acarina, their food supply, breeding grounds or habitat, as a dilute liquid spray or as a solid dust or dust concentrate.

The active ingredients may also be prepared or formulated separately as wettable powders, emulsifiable concentrates, aqueous or liquid flowables, suspension concentrates or the like and tank mixed in the field with water or other inexpensive liquid for application as an aqueous or liquid spray mixture. The separately formulated compositions may also be applied as separate but sequential spray applications. In such applications the aqueous or liquid spray of arylpyrrolecarbonitrile or arylnitropyrrole is generally first to be applied followed by application of an aqueous or liquid spray containing the arylpyrazolecarboxmide. Sequential spraying of one active ingredient may be undertaken from several minutes to several days after the first active ingredient has been applied, and while it appears to be preferable to apply the arylpyrrolecarbonitrile or arylnitropyrrole as the initial treatment, followed by an application of the arylpyrazolecarboxamide as the secondary treatment, if desired, the order of application of the active ingredients may be reversed.

A typical wettable powder formulation containing both the arylpyrrolecarbonitrile and the arylpyrazolecarboxamide may be prepared by grinding together about 1.0% to 7.0% by weight of the arylpyrrolecarbonitrile, preferably 4-bromo-2-(p-chlorophenyl)-1-(ethoxymethyl)-5-(trifluoromethyl)pyrrole-3-carbonitrile, 4-chloro-2-(p-chlorophenyl)-1-(ethoxymethyl)-5-(trifluoromethyl)pyrrole-3-carbonitrile or 4-bromo-2-(3,5-dichlorophenyl)-1-(ethoxymethyl)-5-(trifluoromethyl)pyrrole-3-carbonitrile; about 1.0% to 14.0% by weight of the arylpyrazolecarboxamide, preferably N-(p-tert-butylbenzyl)-4-chloro-3-ethyl-1-methylpyrazole-5-carboxamide; with about 3% to 20% by weight of a surfactant or surfactant mixture, for example, an anionic surfactant such as the dioctyl ester of sodium sulfosuccinic acid alone or in combination with a nonionic surfactant such as a block copolymer of ethylene oxide and propylene oxide; and 60% to 95% by weight of an inert solid diluent such as kaolin, montmorillonite, diatomaceaus earth, a attapulgite, talc or the like.

Typical suspension concentrates of the pyrrolecarbonitrile and the pyrazolecarboxamide may be prepared as separate and distinct compositions by blending together in a high shear blender the following ingredients:

| Pyrrolecarbonitrile Suspension Concentrate Formulation | |
|---|---|
| | % W/V |
| 4-Bromo-2-(p-Chlorophenyl)-1-(ethoxymethyl)-5-(trifluoromethyl)pyrrole-3-carbonitrile; 4-chloro-2-(p-chlorophenyl)-1-(ethoxymethyl)-5-(trifluoromethyl)pyrrole-3-carbonitrile or 2-bromo-2-(3,5-difluorophenyl)-1-(ethoxymethyl)-5-(trifluoromethyl)pyrrole-3-carbonitrile | 24.06 |
| Sodium naphthalene formaldehyde condensate | 2.50 |
| Octylphenoxy polyethoxy ethanol | 0.30 |
| Propylene glycol | 7.50 |
| Aqueous dipropylene glycol solution of 1,2-benzisothiazolin-3-one | 0.10 |
| Silicone antifoam | 0.50 |
| Xanthan gum | 0.20 |
| Magnesium aluminum silicate | 0.20 |
| Water | 64.64 |
| | 100.00 |

| Pyrazole Carboxamide Suspension Concentrate Formulation | |
|---|---|
| | % W/V |
| N-(p-tert-butylbenzyl)-4-chloro-3-ethyl-1-methyl-pyrazole-5-carboxamide | 20.0 |
| Anionic/nonionic surfactant POE alkylaryl ether POE sorbitan alkylate and alkylaryl sulfonate | 10.0 |
| Alkylnophthlene, dialkylnophthalene, acenaphthene, petroleum distillates | 70.0 |
| | 100.0 |

In practice the above-identified formulations are tank mixed in water and applied to plant foliage or insect and acarina habitat as a dilute aqueous spray. The formulation may also be separately tank mixed and applied sequentially to insect and acarina pests or to their habitat or food supply. The sprays may also be applied to plant foliage to protect them from attack by said pests.

The arylnitropyrroles and arylpyrrolecarbonitriles useful in the invention have the structure of formula I below:

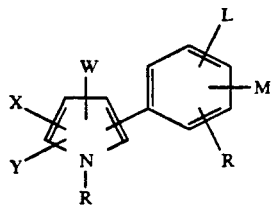
(I)

wherein
X is H, F, Cl, Br, I, or $CF_3$;
Y is H, F, Cl, Br, I, $CF_3$ or CN;
W is CN or $NO_2$;
A is
- H, $C_1$-$C_4$ alkyl or $C_2$-$C_4$ monohaloalkyl, each optionally substituted with from one to three additional halogen atoms, one cyano, one hydroxy, one or two $C_1$-$C_4$ alkoxy groups each optionally substituted with one to three halogen atoms, one $C_1$-$C_4$ alkylthio, one $C_1$-$C_4$ carbalkoxy, one $C_1$-$C_6$ alkylcarbonyloxy, one $C_2$-$C_6$ alkenylcarbonyloxy, one benzenecarbonyloxy, or chloro, dichloro, or methylsubstituted-benzenecarbonyloxy, one phenyl optionally substituted with $C_1$-$C_3$ alkoxy or with one to three halogen atoms, one phenoxy optionally substituted with one to three halogen atoms, or one benzyloxy optionally substituted with one halogen substituent;
- $C_3$-$C_4$ alkenyl optionally substituted with one to three halogen atoms;
- cyano;
- $C_3$-$C_4$ alkynyl optionally substituted with one halogen atom;
- di-($C_1$-$C_4$ alkyl)aminocarbonyl;
- $C_3$-$C_6$ polymethyleneiminocarbonyl;

L is H, F, Cl or Br; and
M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$; and when M and r are on adjacent positions and taken with the carbon atoms to which they are attached they may form a ring in which MR represents the structure:

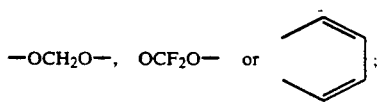

Z is $S(O)n$ or O;
$R_1$ is H, F, $CHF_2$, CHFCl, or $CF_3$;
$R_2$ is $C_1$-$C_3$ alkyl, $C_1$-$C_3$ alkoxy, or $NR_3R_4$;
$R_3$ is H or $C_1$-$C_3$ alkyl;
$R_4$ is H, $C_1$-$C_3$ alkyl, or $R_5CO$;
$R_5$ is H or $C_1$-$C_3$ alkyl; and
n is an integer of 0, 1 or 2.

The arylpyrazolecarboxamides that are useful in the preparation of the synergistic compositions of this invention have the structure of formula II:

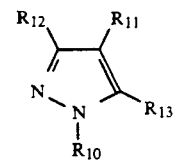
(II)

wherein
$R_{10}$ represents a hydrogen atom, $C_1$-$C_4$ alkyl, $C_1$-$C_4$ haloalkyl, phenyl or benzyl;
one of $R_{12}$ and $R_{13}$ represents

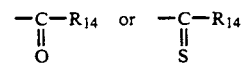

wherein
$R_{14}$ represents

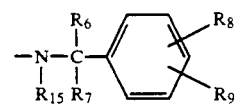

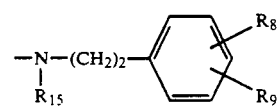

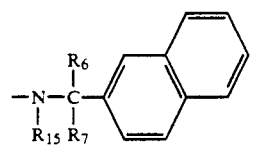

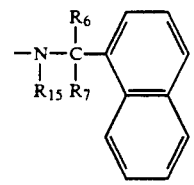

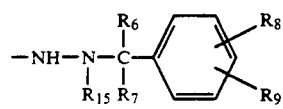

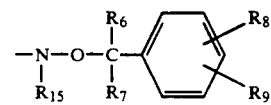

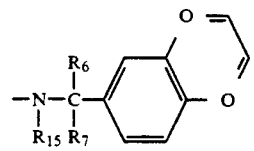

-continued

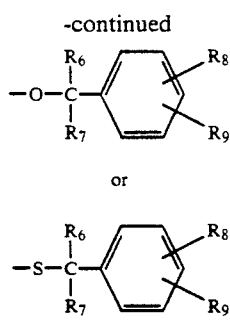

wherein $R_6$, $R_7$ and $R_{15}$ each represent hydrogen, $C_1$-$C_4$ alkyl or phenyl;

$R_8$ and $R_9$ each represent hydrogen, halogen, $C_1$-$C_8$ alkyl, $C_3$-$C_5$ alkenyl, $C_3$-$C_5$ alkynyl, $C_3$-$C_6$ cycloalkyl, $C_2$-$C_4$ alkoxyalkyl, $C_1$-$C_4$ alkoxy, $C_1$-$C_4$ haloalkoxy, nitro, trifluoromethyl, phenyl, benzyl, phenoxy, benzyloxy, amino, $C_1$-$C_4$ alkylamino, cyano, $C_2$-$C_8$ dialkylamino; carboxyl, $C_2$-$C_5$ alkoxycarbonyl, $C_4$-$C_7$ cycloalkoxycarbonyl, $C_3$-$C_9$ alkoxyalkoxycarbonyl, $C_2$-$C_6$ alkylaminocarbonyl, $C_3$-$C_{11}$ dialkylaminocarbonyl, piperidinocarbonyl, morpholinocarbonyl, trimethylsilyl, $C_1$-$C_4$ alkylthio, $C_1$-$C_4$ alkylsulfinyl or $C_1$-$C_4$ alkylsulfonyl; $R_{11}$ is hydrogen, halogen, $C_1$-$C_4$ alkyl, nitro, cyano, $C_1$-$C_5$ alkylamino, $C_2$-$C_{10}$ dialkylamino or $C_2$-$C_7$ acylamino; providing that when all of $R_6$, $R_7$, $R_8$ and $R_9$ are hydrogen atoms, then $R_{10}$ is $C_1$-$C_4$ alkyl, $C_1$-$C_4$ haloalkyl, phenyl or benzyl; and the other of $R_{12}$ and $R_{13}$ represents hydrogen, $C_1$-$C_4$ alkyl, $C_1$-$C_4$ haloalkyl, $C_3$-$C_6$ cycloalkyl or phenyl.

Preferred synergistic compositions contain (A) a formula I arylpyrrolecarbonitrile wherein W is cyano and on the carbon in the 3-position of the pyrrole ring; X is halo and Y is $CF_3$; A is $C_1$-$C_4$ alkyl substituted with $C_1$-$C_4$ alkoxy; L is hydrogen and M and R are each, independently, hydrogen or halogen; and (B) a formula II arylpyrazolecarboxamide wherein $R_{10}$ is hydrogen or $C_1$-$C_4$ alkyl; $R_{12}$ is $C_1$-$C_4$ alkyl; $R_{13}$ is

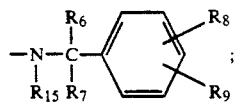

$R_6$, $R_7$ and $R_{15}$ are each independently, hydrogen or $C_1$-$C_4$ alkyl and $R_8$ and $R_9$ are each independently, hydrogen, halogen or $C_1$-$C_4$ alkyl.

A more preferred synergistic composition contains as the essential active ingredients 4-bromo-2-(p-chlorophenyl)-1-(ethoxymethyl)-5-(trifluoromethyl)-pyrrole-3-carbonitrile and N-(p-tert-butylbenzyl)-4-chloro-3-ethyl-1-methylpyrazole-5-carboxamide. This combination of pyrrole carbonitrile and pyrazolecarboxamide provides extremely effective insect control and synergistic miticidal activity. As such, this combination of insecticide and miticide affords ecological advantage over the use of either compound alone since the combination provides essentially complete control of mites and excellent control of insects at substantially lower dosages of insecticidal and miticidal agent than would be required with the application of either compound alone.

Other pyrrole-3-carbonitriles that may be substituted for 4-bromo-2-(p-chlorophenyl)-1-(ethoxymethyl)-5-(trifluoromethyl)pyrrole-3-carbonitrile in the above-identified synergistic composition are: 4-chloro-2-(p-chlorophenyl)-1-(ethoxymethyl)-5-(trifluoromethyl)-pyrrole-3-carbonitrile and 4-bromo-2-(3,5-difluorophenyl)-1-(ethoxymethyl)-5-(trifluoromethyl)-pyrrole-3-carbonitrile.

In practice, it has been found that the pyrazolecarboxamide to pyrrolecarbonitrile or nitropyrrole ratio of from about 1:1 to 2:1 are synergistic when applied as a combination treatment or sequential treatments at rates equivalent to from about 0.025 kg/ha to 0.8 kg/ha and preferably from about 0.03 kg/ha to 0.4 kg/ha of each compound.

The compositions of the invention are superior contact and stomach poisons and are especially useful for protecting growing plants, including: leguminous crops such as soybeans, snap beans, peas, wax beans and the like as well as cotton, forage crops, cole crops, leafy vegetables, tobacco, hops, tomatoes, flowering ornamentals such as chrysanthemums, vine crops such as grapes, squash, pumpkin and melons and fruit trees such as cherry, peach, apple and citrus fruits, from the ravages of insects and mites.

The synergistic mixtures of the present invention are effective against the eggs and the mobile life stages of insects and acarina. They are found to be highly active against a wide variety of insects and acarina and are especially effective for controlling *Panonchus ulmi; Psylla pyricola; Aphis gossypii; Myzus persicae; Phorodon humili; Bemisia persicae; Acubus schlechtendali; Tetronchus urticae; Epitrimerus pyri; Eutetranchus banksii; Phyllocoptruta oleivora; Phorodon humili; Eotetranychus carpini.*

These and other advantages of the present invention may become more apparent from the examples provided below. These examples are provided simply as illustrations of the invention and are not intended as limitations of the present invention.

EXAMPLE 1

Preparation of 4-bromo-2-(p-chlorophenyl)-1-(ethoxymethyl)-5-(trifluoromethyl)pyrrole-3-carbonitrile To 1,000 mL of dry tetrahydrofuran (THF) is added 130.8 g of 4-bromo-2-(p-chlorophenyl)-5-(trifluoromethyl)pyrrole-3-carbonitrile. The mixture is stirred and 43.3 g of potassium t-butoxide is added thereto in several portions causing an exotherm to occur. The exotherm is controlled by cooling the reaction flask in a water bath.

To the stirred mixture 36.5 g of chloromethyl ethyl ether is added in two portions. The reaction progress is then followed by thin layer chromatography.

After about 4 hours, the reaction mixture is diluted with 300 mL of ether and washed with dilute HCl and water. The organic phase is separated, dried over magnesium sulfate, filtered and concentrated in vacuo to give 122 g of the title product. Recrystallization from 500 mL of isopropyl alcohol affords 102 g of the title product as a colorless solid, mp 99°–100° C.

Following the above procedure, but substituting 4-chloro-2-(p-chlorophenyl)-5-(trifluoromethyl)-pyrrole-3-carbonitrile for 4-bromo-2-(p-chlorophenyl)-5-(trifluoromethyl)pyrrole-3-carbonitrile yields 4-chloro-2-(p-chlorophenyl)-1-(ethoxymethyl)-5-(trifluoromethyl)-pyrrole-3-carbonitrile, mp 104.0°–104.5° C.

EXAMPLE 2

Preparation of 4,5-dichloro-2-(3,4-dichlorophenyl)-1-(1-ethoxyethyl)-pyrrole-3-carbonitrile To 4,5-dichloro-2-(3,4-dichlorophenyl)-pyrrole-3-carbonitrile (5.0 g, 0.016 mol) dissolved in 300 mL of tetrahydrofuran is added, portionwise, potassium t-butoxide (2.75 g, 0.025 mol) with ice cooling and stirring. The cooled mixture is treated with a solution of 1-chloroethyl ethyl ether (2.31 g, 0.021 mol) in 15 mL of tetrahydrofuran at 10° C. over a 5 minute period. The mixture is stirred for ½ hour at ambient temperatures, evaporated to a volume of 50 mL and poured into a mixture of 200 mL of ethyl acetate and 100 mL of water. The organic layer is separated, washed with water (2×100 mL), saturated NaCl solution (1×100 mL), dried over anhydrous magnesium sulfate and evaporated to give the title product 5.9 g, mp 124°–126° C.

Following the above procedure but using the appropriately substituted phenylpyrrole-3-carbonitrile and appropriate alkylating agent gives 4-bromo-2-(3,5-difluorophenyl)-1-(ethoxymethyl)-5-(trifluoromethyl)-pyrrole-3-carbonitrile, mp 74°–75° C.

EXAMPLE 3

Preparation of N-(p-tert-butylbenzyl)-4-chloro-3-ethyl-1-methyl-pyrazole-5-carboxamide A mixture of ethyl 4-chloro-3-ethyl-1-methyl-pyrazole-5-carboxamide and 4-tert-butylbenzylamine is heated to 200° C. for four hours with continuous stirring. Thereafter the reaction mixture is cooled to room temperature and the reaction mixture purified by silica gel chromatography to obtain the desired product 115°–117° C.

EXAMPLE 4

Evaluation of the combination of 4-bromo-2-(p-chlorophenyl)-1-(ethoxymethyl)-5-(trifluoromethyl)pyrrole-3-carbonitrile and N-(p-tert-butylbenzyl)-4-chloro-3-ethyl-1-methyl-pyrazole-5-carboxamide for enhanced activity against the two-spotted spider mite (*Tetranychus urticae*)

These tests are conducted to evaluate the combination of 4-bromo-2-(p-chlorophenyl)-1-(ethoxy methyl)-5-(trifluoromethyl)pyrrole-3-carbonitrile and N-(p-tert-butylbenzyl)-4-chloro-3-ethyl-1-methylpyrazole-5-carboximide for enhanced activity over the maximum activity expected for either compound alone against the two-spotted spider mite (*Tetranychus utricae*). The tests are conducted by three different individuals using a 3-second leaf-dip test with acetone-water (50:50) as the solvent system. The test solutions are prepared by dissolving the appropriate amount of test compound or compounds in the acetone-water mixture. Sieva lima bean plants with primary leaves expanded to 7–8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is removed and discarded. The mite-infested plants are then dipped in the test formulation, agitated for 3 seconds and set in the hood to dry. Plants are kept for 3 days before estimates of adult kill is made.

Data obtained are reported in tables I, II and III below.

TABLE I

Synergistic effectiveness of the combination of 4-bromo-2-(p-chlorophenyl)-1-(ethoxymethyl)-5-(trifluoromethyl)pyrrole-3-carbonitrile and N-(p-tert-butylbenzyl)-4-chloro-3-ethyl-1-methylpyrazole-5-carboxamide against the two-spotted spider mite (*Tetranychus urticae*)

| 4-Bromo-2-(p-chlorophenyl)-1-(ethoxymethyl)-5-(trifluoromethyl)pyrrole-3-carbonitrile Concn. in PPM | N-(p-tert-butylbenzyl)-4-chloro-3-ethyl-1-methylpyrazole-5-carboxamide Concn. in PPM | Percent Mortality 3 DAT |
|---|---|---|
| 4.6 | — | 99.8 |
| 2.7 | — | 95.5 |
| 1.52 | — | 56.0 |
| 0.88 | — | 23.3 |
| 0.50 | — | 17.2 |
| 0.29 | — | 13.6 |
| — | 4.6 | 96.4 |
| — | 2.7 | 77.4 |
| — | 1.52 | 26.5 |
| — | 0.88 | 15.7 |
| — | 0.50 | 5.4 |
| — | 0.29 | 1.3 |
| 2.3 | 2.3 | 99.5 |
| 1.35 | 1.35 | 99.7 |
| 0.76 | 0.76 | 80.0 |
| 0.44 | 0.44 | 34.0 |
| 0.25 | 0.25 | 10.1 |
| 0.145 | 0.145 | 12.9 |
| Check | | 3.0 |

TABLE II

Synergistic effectiveness of the combination of 4-bromo-2-(p-chlorophenyl)-1-(ethoxymethyl)-5-(trifluoromethyl)pyrrole-3-carbonitrile and N-(p-tert-butylbenzyl)-4-chloro-3-ethyl-1-methylpyrazole-5-carboxamide against the two-spotted spider mite (*Tetranychus urticae*)

| 4-Bromo-2-(p-chlorophenyl)-1-(ethoxymethyl)-5-(trifluoromethyl)pyrrole-3-carbonitrile Concn. in PPM | N-(p-tert-butylbenzyl)-4-chloro-3-ethyl-1-methylpyrazole-5-carboxamide Concn. in PPM | Percent Mortality 3 DAT |
|---|---|---|
| 7.8 | — | 94.6 |
| 4.2 | — | 98.7 |
| 2.3 | — | 87.0 |
| 1.25 | — | 52.2 |
| 0.68 | — | 30.0 |
| 0.34 | — | 14.1 |
| — | 7.8 | 97.7 |
| — | 4.2 | 93.8 |
| — | 2.3 | 57.6 |
| — | 1.25 | 76.8 |
| — | 0.68 | 31.7 |
| — | 0.34 | 8.7 |
| 2.3 | 2.3 | 100.0 |
| 1.35 | 1.35 | 99.6 |
| 0.76 | 0.76 | 82.0 |
| 0.44 | 0.44 | 69.8 |
| 0.25 | 0.25 | 23.2 |
| 0.145 | 0.145 | 10.6 |
| Check | | 3.0 |

TABLE III

Synergistic effectiveness of the combination of

TABLE III-continued

Evaluation of 4-bromo-2-(p-chlorophenyl)-1-(ethoxymethyl)-5-(trifluoromethyl)pyrrole-3-carbonitrile and N-(p-tert-butylbenzyl)-4-chloro-3-ethyl-1-methylpyrazole-5-carboxamide against the two-spotted spider mite (*Tetranychus urticae*)

| 4-Bromo-2-(p-chlorophenyl)-1-(ethoxymethyl)-5-(trifluoromethyl)pyrrole-3-carbonitrile Concn. in PPM | N-(p-tert-butylbenzyl)-4-chloro-3-ethyl-1-methylpyrazole-5-carboxamide Concn. in PPM | Percent Mortality 3 DAT |
|---|---|---|
| 7.8 | — | 100.0 |
| 4.2 | — | 100.0 |
| 2.3 | — | 89.0 |
| 1.25 | — | 50.0 |
| 0.68 | — | 16.0 |
| 0.34 | — | 5.0 |
| — | 7.8 | 98.0 |
| — | 4.2 | 86.0 |
| — | 2.3 | 41.0 |
| — | 1.25 | 7.0 |
| — | 0.68 | 0 |
| — | 0.34 | 2.0 |
| 3.9 | 3.9 | 100.0 |
| 2.1 | 2.1 | 99.8 |
| 1.15 | 1.15 | 95.2 |
| 0.625 | 0.625 | 68.7 |
| 0.34 | 0.34 | 25.8 |
| 0.17 | 0.17 | 6.8 |
| Check | | 3.0 |

EXAMPLE 5

Evaluation of a pyrrole carbonitrile, a pyrazle carboxamide and the combination thereof against the two spotted spider mite (*Tetranychus urticae*)

In the tests the active materials are diluted with deionized water to the desired concentration and sprayed with a volume of 400 L/ha at 40 psig. The foliage of young sieva lima bean plants is sprayed with test solution when the plants are placed on a moving belt and passed under a spray head equipped with a flat tip. The plants are approximately 20 cm in height and the nozzle tip is mounted about 66 cm above the belt.

After spraying, the plants are permitted to dry. A subsample is infested with mites and the remaining plants are placed on greenhouse benches under high intensity discharge lamps. The plants are subsampled at various time intervals and infested with mites using a half-inch square of bean leaf containing about 100 mites from the rearing culture. The infested plants are placed in the holding room at 26.5°±1° C. and 40±10% relative humidity. Mortality counts are made 3 days after mite transfer and infestations are made up to 14 days after plant spraying to evaluate the residual activity of the test compounds and the combination.

Rates tested are 0.04 kg/ha and 0.08 kg/ha.

Data obtained are reported in tables IV and V below.

In these tests compound A is N-(p-tert-butylbenzyl)-4-chloro-3-ethyl-1-methylpyrazole-5-carboxamide; compound B is 4-bromo-2-(p-chlorophenyl)-1-(ethoxymethyl)-5-(trifluoromethyl)pyrrole-3-carbonitrile.

TABLE IV

Synergistic Effectiveness of the Combination of a pyrrole and a pyrazole Against Two-spotted Spider Mites (*Tetranychus urticae*) on Sieva Lima Bean Plants

| compound | kg ai/ha | compound | kg ai/ha | 3-Day Percent Mortality* Post-infestation at DAT | | | | |
|---|---|---|---|---|---|---|---|---|
| | | | | 0 | 4 | 7 | 11 | 14 |
| A | 0.08 | — | — | 96 | 0 | 0 | — | 0 |
| — | — | B | 0.04 | 85 | 99 | 60 | 58 | 44 |
| A | 0.08 | B | 0.04 | 100 | 100 | 100 | 96 | 97 |

TABLE V

Synergistic Effectiveness of the Combination of a pyrrole and a pyrazole Against Two-spotted Spider Mites (*Tetranychus urticae*) on Sieva Lima Bean Plants

| compound | kg ai/ha | compound | kg ai/ha | 3-Day Percent Mortality* Post-infestation at DAT | | | |
|---|---|---|---|---|---|---|---|
| | | | | 0 | 3 | 7 | 14 |
| A | 0.04 | — | — | 38 | 1 | 3 | 1 |
| — | — | B | 0.04 | 100 | 89 | 79 | 73 |
| A | 0.04 | B | 0.04 | 100 | 100 | 99 | 96 |

From these tests it may be seen that the combination of the pyrazole and the pyrrole in a ratio of 2:1, respectively, is approximately 1.7 times more effective than either compound alone. The same combination in a ratio of 1:1 is about 1.3 times more effective than either compound alone.

What is claimed is:

1. A synergistic miticidal composition comprising as essential active ingredients a synergistically effective amount of an arylnitropyrrole or arylpyrrolecarbonitrile having the structure of formula I:

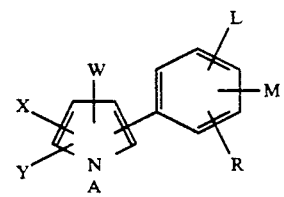

wherein
X is H, F, Cl, Br, I, or CF$_3$;
Y is H, F, Cl, Br, I, CF$_3$ or CN;
W is CN or NO$_2$;
A is H, C$_1$-C$_4$ alkyl or C$_2$-C$_4$ monohaloalkyl, each optionally substituted with from one to three additional halogen atoms, one cyano, one hydroxy, one or two C$_1$-C$_4$ alkoxy groups each optionally substituted with one to three halogen atoms, one C$_1$-C$_4$ alkylthio, one C$_1$-C$_4$ carbalkoxy, one C$_1$-C$_6$ alkylcarbonyloxy one C$_2$-C$_6$ alkenylcarbonyloxy, one benzenecarbonyloxy or chloro, dichloro or methylsubstituted-benzenecarbonyloxy, one phenyl optionally substituted with C$_1$-C$_3$ alkoxy or with one to three halogen atoms, one phenoxy optionally substituted with one to three halogen atoms or one benzyloxy optionally substituted with one halogen substituent; C$_3$-C$_4$ alkenyl optionally substituted with one to three halogen atoms; cyano, C$_3$-C$_4$ alkynyl optionally substituted with one halogen atom, di-(C$_1$-C$_4$ alkyl) aminocarbonyl, C$_3$-C$_6$ polymethyleneiminocarbonyl;
L is H, F, Cl or Br; and
M and R are each independently H$_1$, C$_1$-C$_3$ alkyl, C$_1$-C$_3$ alkoxy, C$_1$-C$_3$ alkylthio, C$_1$-C$_3$ alkylsulfinyl, C$_1$-C$_3$ alkylsulfonyl, cyano, F, Cl, Br, I, nitro, CF$_3$, R$_1$CF$_2$Z, R$_2$CO or NR$_3$R$_4$; and when M and R are on adjacent positions and taken with the carbon atoms to which they are attached they may form a ring in which MR represents the structure:

—OCH$_2$O—, OCF$_2$O— or 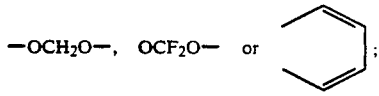 ;

Z is S(O)n or O;
R$_1$ is H, F, CHF$_2$, CHFCl, or CF$_3$;
R$_2$ is C$_1$-C$_3$ alkyl, C$_1$-C$_3$ alkoxy, or NR$_3$R$_4$;
R$_3$ is H or C$_1$-C$_3$ alkyl;
R$_4$ is H, C$_1$-C$_3$ alkyl, or R$_5$CO;
R$_5$ is H or C$_1$-C$_3$ alkyl; and
n is an integer of 0, 1 or 2;
and an arylpyrazolecarboxamide having the structure of formula II:

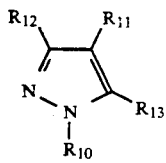 (II)

wherein
R$_{10}$ represents a hydrogen atom, C$_1$-C$_4$ alkyl, C$_1$-C$_4$ haloalkyl, phenyl or benzyl;
one of R$_{12}$ and R$_{13}$ represents

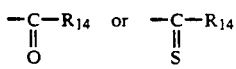

wherein R$_{14}$ represents

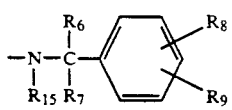

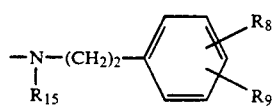

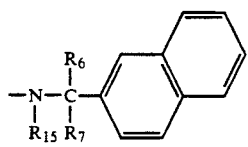

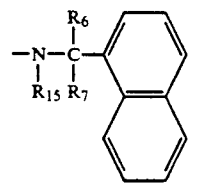

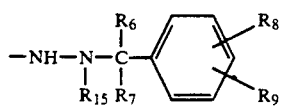

-continued

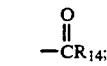

wherein
R$_6$, R$_7$ and R$_{15}$ each represent hydrogen, C$_1$-C$_4$ alkyl or phenyl;
R$_8$ and R$_9$ each represent hydrogen, halogen, C$_1$-C$_8$ alkyl, C$_3$-C$_5$ alkenyl, C$_3$-C$_5$ alkynyl, C$_3$-C$_6$ cycloalkyl, C$_2$-C$_4$ alkoxyalkyl, C$_1$-C$_4$ alkoxy, C$_1$-C$_4$ haloalkoxy, nitro, trifluoromethyl, phenyl, benzyl, phenoxy, benzyloxy, amino, C$_1$-C$_4$ alkylamino, cyano, C$_2$-C$_8$ dialkylamino, carboxyl, C$_2$-C$_5$ alkoxycarbonyl, C$_4$-C$_7$ cycloalkoxycarbonyl, C$_3$-C$_9$ alkoxyalkoxycarbonyl, C$_2$-C$_6$ alkylaminocarbonyl, C$_3$-C$_{11}$ dialkylaminocarbonyl, piperidinocarbonyl, morpholinocarbonyl, trimethylsilyl, C$_1$-C$_4$ alkylthio, C$_1$-C$_4$ alkylsulfinyl or C$_1$-C$_4$ alkylsulfonyl;
R$_{11}$ is hydrogen, halogen, C$_1$-C$_4$ alkyl, nitro, cyano, C$_1$-C$_5$ alkylamino, C$_2$-C$_{10}$ dialkylamino or C$_2$-C$_7$ acylamino;
providing that when all of R$_6$, R$_7$, R$_8$ and R$_9$ are hydrogen atoms, then R$_{10}$ is C$_1$-C$_4$ alkyl, C$_1$-C$_4$ haloalkyl, phenyl or benzyl; and the other of R$_{12}$ and R$_{13}$ represents hydrogen, C$_1$-C$_4$ alkyl, C$_1$-C$_4$ haloalkyl, C$_3$-C$_6$ cycloalkyl or phenyl wherein the ratio of the formula II compound to the formula I compound in the synergistic composition is between about 1:1 and 2:1.

2. The composition according to claim 1 wherein the formula I compound is an arylpyrrolecarbonitrile wherein W is cyano and on the carbon in the 3-position of the pyrrole ring; X is halo and Y is CF$_3$; A is C$_1$-C$_4$ alkyl substituted with C$_1$-C$_4$ alkoxy; L is hydrogen and M and R are each, independently, hydrogen or halogen; and the formula II compound is an arylpyrazolecarboxamide wherein R$_{10}$ is hydrogen or C$_1$-C$_4$ alkyl; R$_{12}$ is C$_1$-C$_4$ alkyl; R$_{13}$ is $$-\overset{O}{\underset{\|}{C}}R_{14};$$

R$_{14}$ is

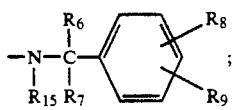

$R_6$, $R_7$ and $R_{15}$ are each independently, hydrogen or $C_1$–$C_4$ alkyl and $R_8$ and $R_9$ are each independently, hydrogen, halogen or $C_1$–$C_4$ alkyl.

3. The composition according to claim 1 wherein the formula I compound is 4-bromo-2-(p-chlorophenyl)-1-(ethoxymethyl)-5-(trifluoromethyl)pyrrole-3-carbonitrile and the formula II compound is N-(p-tert-butylbenzyl)-4-chloro-3-ethyl-1-methylpyrazole-5-carboxamide.

4. The composition according to claim 1 wherein the formula I compound is 4-chloro-2-(p-chlorophenyl)-1-(ethoxymethyl)-5-(trifluoromethyl)pyrrole-3-carbonitrile and the formula II compound is N-(p-tert-butylbenzyl)-4-chloro-3-ethyl-1-methylpyrazole-5-carboxamide.

5. The composition according to claim 1 wherein the formula I compound is 4-bromo-2-(3,5-difluorophenyl)-1-(ethoxymethyl)-5-(trifluoromethyl)pyrrole-3-carbonitrile and the formula II compound is N-(p-tert-butylbenzyl)-4-chloro-3-ethyl-1-methylpyrazole-5-carboxamide.

6. The composition according to claim 1 wherein the composition contains sufficient active ingredient to provide about 0.025 kg/ha to 0.8 kg/ha of each formula I and formula II compound.

7. The composition according to claim 1 wherein the composition contains sufficient active ingredient to provide about 0.03 kg/ha to 0.4 kg/ha of each formula I and formula II compound.

8. The composition according to claim 1 wherein the composition contains sufficient active ingredient to provide in total about 0.05 kg/ha to 2.4 kg/ha of the formula I and formula II compounds.

* * * * *